United States Patent
Kato et al.

(10) Patent No.: US 7,067,642 B1
(45) Date of Patent: Jun. 27, 2006

(54) HUMAN NUCLEAR PROTEIN HAVING WW DOMAIN AND POLYNUCLEOTIDE ENCODING THE SAME

(75) Inventors: Seishi Kato, Kanagawa (JP); Akihiko Komuro, Kanagawa (JP); Yutaka Hirose, Ishikawa (JP)

(73) Assignee: Japan Science and Technology Corporation, Saitama (JP)

( * ) Notice: Subject to any disclaimer, the term of this patent is extended or adjusted under 35 U.S.C. 154(b) by 144 days.

(21) Appl. No.: 09/889,722

(22) PCT Filed: Nov. 22, 2000

(86) PCT No.: PCT/JP00/08253

§ 371 (c)(1),
(2), (4) Date: Oct. 19, 2001

(87) PCT Pub. No.: WO01/38531

PCT Pub. Date: May 31, 2001

(30) Foreign Application Priority Data

Nov. 24, 1999  (JP)  ................................. 11/332572

(51) Int. Cl.
*C07H 21/02* (2006.01)
*C07H 21/04* (2006.01)
*C12N 15/00* (2006.01)
*C12N 15/09* (2006.01)
*C12N 5/00* (2006.01)

(52) U.S. Cl. .................. 536/23.1; 435/320.1; 435/325
(58) Field of Classification Search ............... 536/23.1; 435/325, 320.1
See application file for complete search history.

(56) References Cited

OTHER PUBLICATIONS

Chen et al. Charicterization of the WW domain of human Yes-associated protein and its polyproline containing ligands JBC Vo.272 No. 27, 1997 pp. 17070-17077.*
P. Morris et al., "Phospho-Carboxyl-Terminal Domain Binding and the Role of a Prolyl Isomerase in Pre-mRNA 3'-End Formation", Journal of Biological Chemistry, vol. 274, No. 44, Oct. 1999, pp. 31583-31587.
EMBL/GenBank/DDBJ, Accession No. AL137437.

* cited by examiner

*Primary Examiner*—James Ketter
*Assistant Examiner*—Konstantina Katcheves
(74) *Attorney, Agent, or Firm*—Wenderoth, Lind & Ponack, L.L.P.

(57) ABSTRACT

An isolated and purified human nucleoprotein containing the amino acid sequence of SEQ ID NO:1; a polynucleotide encoding this protein; and an antibody against this protein. The above protein and antibody are useful in diagnosing and treating the pathogenic conditions of cancer, etc. The above polynucleotide is usable in acquiring the protein in a large amount. By screening a low-molecular weight compound binding to this protein, drugs of a novel type (antitumor agents, etc.) can be searched for.

6 Claims, No Drawings

HUMAN NUCLEAR PROTEIN HAVING WW DOMAIN AND POLYNUCLEOTIDE ENCODING THE SAME

This application is a 371 of PCT/JP00/08253 filed Nov. 22, 2000.

TECHNICAL FIELD

The present invention relates to a novel protein having a WW domain and existing in human cell nuclei, a polynucleotide encoding this protein, and an antibody against this protein. The protein and antibody of the present invention are useful for diagnosis and therapy of various diseases, and the polynucleotide of the present invention is useful as a probe for genetic diagnosis or as a genetic source for gene therapy. Further, the polynucleotide can be used as a genetic source for large-scale production of the protein of this invention.

BACKGROUND ART

The term "nuclear protein" is a generic name of proteins functioning in cell nucleus. In nucleus there are genomic DNA serving as a plan of organism, and nuclear proteins are involved in replication, transcriptional regulation etc. of these genomic DNA. Typical nuclear proteins whose functions have been revealed include a transcription factor, a splicing factor, an intranuclear receptor, a cell cycle regulator and a tumor suppressor. These factors are closely related not only to life phenomena such as development and differentiation but also to diseases such as cancers (New Medical Science, "Tensha No Shikumi To Shikkan" (Mechanism of Transcription and Diseases) ed. by Masahiro Muramatsu). Accordingly, these nuclear proteins are expected as target proteins for developing low-molecular pharmaceutical preparations that regulate transcription and translation of specific genes, and it is desired to obtain as many nuclear proteins as possible.

The WW domain belongs to a new family of protein—protein interaction motifs resembling SH2, SH3, PH and PTB domains. It is known that this domain consists of about 40 amino acid residues containing 2 conserved tryptophan residues, and like the SH3 domain, binds to a proline-rich amino acid sequence (H. I. Chen and M. Sudol., Proc. Natl. Sci. 92, 7819–7823, 1995). As a result of X-ray crystallographic analysis of a WW domain/ligand conjugate, it was revealed that the three-dimensional structure of the WW domain is different from that of SH3 (M. J. Macias et al., Nature, 382, 646–649, 1996). Like other protein motifs, the WW domain is contained in the cytoskeleton system (P. Bork and M. Sudol TIBS, 19, 531–533, 1994), in proteins participating in the signal transduction system (H. I. Chen and M. Sudol., Proc. Natl. Sci., 92, 7819–7823, 1995), in a ubiquitin-protein ligase in the protein degradation system (O. Staub et al., EMBO J., 15, 2371–2380, 1996) and in a transcription activator (P. Bork and M. Sudol, TIBS, 19, 531–533, 1994), and is believed to play an important role in the intracellular signal transduction system.

The object of the present invention is to provide a novel protein present in human cell nucleus, a polynucleotide encoding this protein, and an antibody against this nuclear protein.

DISCLOSURE OF INVENTION

To achieve the object described above, the present application provides the following inventions (1) to (7):

(1) An isolated and purified human nuclear protein comprising the amino acid sequence of SEQ ID NO: 1.

(2) A polynucleotide encoding the protein of the invention (1), which comprises the nucleotide sequence of SEQ ID NO: 2.

(3) The polynucleotide of the invention (2), consisting of the nucleotide sequence of SEQ ID NO: 2.

(4) A human genomic DNA fragment with which a polynucleotide of SEQ ID NO:3 or a partial contiguous sequence thereof hybridizes under stringent conditions.

(5) An expression vector expressing the polynucleotide of the invention (2) or (3) in in vitro translation or in host cells.

(6) A transformed cell producing the human nuclear protein of the invention (1), which is transformant with the expression vector of the invention (5).

(7) An antibody against the human nuclear protein of the invention (1).

BEST MODE FOR CARRYING OUT THE INVENTION

The protein of the invention (1) can be obtained by a method of isolation thereof from human organs, cell lines etc., by a method of preparing the peptide through chemical synthesis on the basis of the amino acid sequence set forth in SEQ ID NO: 1 or by a method of production thereof by recombinant DNA technique using the polynucleotide encoding the amino acid sequence of SEQ ID NO: 1, among which the method with recombinant DNA technique is preferably used. For example, a vector harboring the polynucleotide of the invention (2) or (3) is subjected to in vitro transcription to prepare RNA which is then used as a template in in vitro translation, whereby the protein can be expressed in vitro. Further, by integrating the polynucleotide in a conventional method into a suitable expression vector, the protein encoded by the polynucleotide can be expressed in a large amount in procaryotes such as *E. coli, Bacillus subtilis* etc. or eucaryotes such as yeasts, insect cells and mammalian cells.

To produce the protein of the invention (1) by expressing the DNA through in vitro translation, the polynucleotide of the invention (2) or (3) is integrated in a vector harboring an RNA polymerase promoter (the invention (5)) and added the vector to an in vitro translation system such as a rabbit reticulocyte lysate or a wheat germ extract containing an RNA polymerase compatible with said promoter, whereby the protein of the invention (1) can be produced in vitro. The RNA polymerase promoter includes e.g. T7, T3 and SP6. The vector harboring such RNA polymerase promoter includes e.g. pKA1, pCDM8, pT3/T7 18, pT7/3 19, and pBluescript II.

To produce the protein of the invention (1) by expressing the DNA in microorganisms such as *E. coli*, the polynucleotide of the invention (2) or (3) is integrated in an expression vector harboring an origin capable of replication in microorganisms, a promoter, a ribosome-binding site, a DNA cloning site, a terminator etc. to prepare the expression vector (the invention (5)) which is then used for transformation of host cells, and by culturing the resulting transformant (the invention (6)), the protein encoded by said polynucleotide can be produced in a large amount in the microorganism. If an initiation codon and a termination codon have been added respectively to sites upstream and downstream from an arbitrary translated region in said expression vector, a protein fragment containing the arbitrary region can be obtained by expressing the DNA. Alternatively, it can also be expressed as a fusion protein with another protein. By cleaving this fusion protein with a suitable protease, the part of only the protein encoded by said polynucleotide can be obtained. The expression vector for *E. coli* includes e.g. pUC series vectors, pBluescript II, pET expression system vectors and pGEX expression system vectors.

To produce the protein of the invention (1) by expressing the DNA in eucaryotes, the translated region of the polynucleotide of the invention (2) or (3) is integrated in an eucaryotic expression vector harboring a promoter, a splicing region, a poly(A)-additional site etc. to prepare the expression vector (the invention (5)) which is then used for transforming eucaryotic cells (the invention (6)), whereby the protein of the invention (1) can be produced in the eucaryotic cells. The expression vector includes e.g. pKAI, pCDM8, pSVK3, pMSG, pSVL, pBK-CMV, pBK-RSV, EBV vector, pRS and pYES2. If vectors such as pIND/V5-His, pFLAG-CMV-2, pEGFP-N1 and pEGFP-C1 are used, the protein of the present invention can also be expressed as a fusion protein having various tags such as His tag, FLAG tag and GFP added thereto. As the eucaryotic cells, mammalian cultured cells such as simian renal cells COS7 and Chinese hamster ovary cells CHO, budding yeasts, fission yeasts, silkworm cells and *Xenopus* oocytes are generally used, but insofar as the protein of the invention (1) can be expressed, any eucaryotic cells can be used. For introducing the expression vector into eucaryotic cells, conventional methods such as the electroporation method, calcium phosphate method, liposome method and DEAE-dextran method can be used.

For isolating and purifying the protein of the invention (1) from a culture after expression of the desired protein in the procaryotic or eucaryotic cells, separation techniques known in the art can be used in combination. Such techniques include e.g. treatment with a denaturant such as urea or a surfactant, sonication, enzymatic digestion, salting-out or solvent precipitation, dialysis, centrifugation, ultrafiltration, gel filtration, SDS-PAGE, isoelectric focusing, ion-exchange chromatography, hydrophobic chromatography, affinity chromatography and reverse phase chromatography.

The protein of the invention (1) encompasses peptide fragments (each consisting of 5 or more amino acid residues) containing any partial amino acid sequence from the SEQ ID NO: 1. Such a peptide fragment can be used as an antigen for preparing the antibody of the present invention. Further, the protein of the invention (1) encompasses fusion proteins with another arbitrary protein. For example, fusion proteins with glutathione-S-transferase (GST) or green fluorescent protein (GFP), described in the Examples, can be mentioned.

The polynucleotide (cDNA) of the invention (2) or (3) can be cloned from a cDNA library derived from e.g. human cells. The cDNA is synthesized using poly(A)+ RNA as a template extracted from human cells. The human cells may be either cultured cells or cells excised by an operation etc. from the human body. The cDNA can be synthesized by any methods such as the Okayama-Berg method (Okayama, H. and Berg, P., Mol. Cell Biol., 2, 161–170, 1982) and the Gubler-Hoffman method (Gubler, U. and Hoffman, J. Gene, 25, 263–269, 1983), but for efficiently obtaining full-length clones, the Capping method (Kato, S. et al., Gene, 150, 243–250, 1994) described in the Examples is preferably used.

The polynucleotide of the invention (2) comprises the nucleotide sequence of SEQ ID NO: 2, and for example, the polynucleotide consisting of the nucleotide sequence of SEQ ID NO: 3 has a 2669-bp nucleotide sequence containing a 2115-bp open reading frame (ORF). This ORF encodes a protein consisting of 704 amino acid residues. The polynucleotide of the invention (3) comprises the 2115-bp nucleotide sequence (SEQ ID NO:2) constituting this ORF. By expressing the cDNA of the invention (2) or (3) in *E. coli* or animal cultured cells, an about 80-kDa protein was obtained. This protein binds to a C-terminal domain of RNA polymerase II, so it is considered to participate in transcriptional regulation.

Since the protein of the invention (1) is expressed in any tissues, the same clone as the polynucleotide of the invention (2) or (3) can be easily obtained from a human cDNA library prepared from human cells by screening the library with an oligonucleotide probe synthesized on the basis of the nucleotide sequence of the polynucleotide set forth in SEQ ID NO: 2 or 3. Alternatively, the objective cDNA can also be synthesized by polymerase chain reaction (PCR) by use of such oligonucleotides as primers.

Generally, polymorphism of human genes occurs frequently due to individual variations. Accordingly, those polynucleotides where in SEQ ID NO: 2 or 3, one or more nucleotides have been added, deleted and/or substituted with other nucleotides fall under the scope of the invention (3) or (4).

Accordingly, those proteins where in SEQ ID NO: 1, one or more amino acids have been added, deleted and/or substituted with other amino acids as a result of such alterations to nucleotides also fall under the scope of the invention (1) insofar as they have the activity of a protein having the amino acid sequence of SEQ ID NO: 1.

The polynucleotide of the invention (2) or (3) encompasses DNA fragments (10 bp or more) containing any partial nucleotide sequence from the sequence of SEQ ID NO: 2 or 3. Further, DNA fragments consisting of a sense or antisense strand thereof fall under the scope of this invention. These DNA fragments can be used as probes for genetic diagnosis.

The invention (4) is concerned with a human genomic DNA fragment with which the polynucleotide of SEQ ID NO: 3 or a partial contiguous sequence thereof hybridizes under stringent conditions. As used herein, the stringent conditions are that enables specific and detectable binding between the polynucleotide of SEQ ID NO: 3 or a partial contiguous sequence thereof (30 bp or more) and chromosome-derived genomic DNA. The stringent conditions are defined in terms of salt concentration, organic solvent (e.g., formamide), temperature and other known conditions. That is, stringency is increased by a decrease in salt concentration, by an increase in organic solvent concentration, or by an increase in hybridization temperature. For example, the stringent salt concentration is usually about 750 mM or less NaCl and about 75 mM or less trisodium citrate, more preferably about 500 mM or less NaCl and about 50 mM or less trisodium citrate and most preferably about 250 mM or less NaCl and about 25 mM or less trisodium citrate. The stringent organic solvent concentration is about 35% or more formamide, most preferably about 50% or more formamide. The stringent temperature condition is about 30° C. or more, more preferably about 37° C. or more and most preferably about 42° C. or more. The other conditions include hybridization time, the concentration of a detergent (e.g. SDS), the presence or absence of carrier DNA, etc., and by combining these conditions, varying stringency can be established. Further, the conditions for washing after hybridization also affects stringency. The washing conditions are also defined in terms of salt concentration and temperature, and the stringency of washing is increased by a decrease in salt concentration or by an increase in temperature. For example, the stringent salt condition for washing is about 30 mM or less NaCl and about 3 mM or less trisodium citrate, most preferably about 15 mM or less NaCl and about 1.5 mM or less trisodium citrate. The stringent temperature condition for washing is about 25° C. or more, more preferably about 42° C. or more and most preferably about 68° C. or more. The genomic DNA fragment of the invention (4) can be isolated for example by subjecting a genome library prepared from human chromosomal DNA to screening by the above stringent hybridization with said polynucleotide as a probe and subsequent washing.

The genomic DNA fragment of the invention (4) comprises expression-regulating regions (promoter/enhancer and suppressor sequences, etc.) for the region coding for the protein of the invention (1). These expression-regulating regions are useful as a material for screening a material regulating in vivo expression of the protein of the invention (1).

The antibody of the invention (7) can be obtained from serum in an animal immunized with the protein of the invention (1) as an antigen. The antigen used may be a peptide chemically synthesized on the basis of the amino acid sequence of SEQ ID NO: 1 or the protein expressed in the eucaryotic or procaryotic cells. Alternatively, the antibody can be prepared by introducing the above-described expression vector for eucaryotic cells through an injection or a gene gun into animal muscles or slin and then collecting serum (e.g., an invention in JP-7-313187A). As the animal, a mouse, rat, rabbit, goat, chicken or the like is used. If a hybridoma is produced by fusing myeloma cells with B cells collected from the spleen in the immunized animal, a monoclonal antibody against the protein of the invention (1) can be produced by the hybridoma.

EXAMPLES

The present invention will be described in more detail by reference to the Examples, which however are not intended to limit the scope of the present invention. Basic procedures for DNA recombination and enzymatic reaction were in accordance with those described in a literature (Molecular Cloning, A Laboratory Manual, Cold Spring Harbor Laboratory, 1989). Unless otherwise specified, the restriction enzymes and various modifying enzymes used were products of Takara Shuzo Co., Ltd. The buffer composition in each enzymatic reaction, as well as reaction conditions, was followed instructions attached to the kits. Synthesis of cDNA was conducted according to a literature (Kato, S. et al., Gene, 150, 243–250, 1994).

(i) cDNA Cloning

As a result of large-scale determination of the nucleotide sequences of cDNA clones selected from a human full-length cDNA library (described in WO97/03190), clone HP03494 was obtained. This clone had a structure made of a 291-bp 5'-untranslated region, a 2115-bp ORF and a 263-bp 3'-untranslated region (SEQ ID NO: 3). The ORF encodes a protein consisting of 704 amino acid residues.

Using the amino acid sequence (SEQ ID NO: 1) of this protein, a protein database was searched, but none of known proteins had homology to this protein. Further examination of GenBank by using the nucleotide sequence of its cDNA indicated that some ESTs (e.g. Accession No. A1758365) have 90% or more homology thereto, but they are partial sequences, so whether or not they code for the same protein as the protein of this invention cannot be judged.

Examination of motif sequences indicated that as shown in Table 1, the region of from the 43- to 78-positions has homology to WW domains. Tryptophan residues at the 49- and 72-positions and a proline residue at the 75-position are amino acid residues conserved in every known WW domain.

TABLE 1

| Protein | Position | Amino Pod Sequence | | Accession No. |
|---|---|---|---|---|
| Conserved Sequence | | ———W————————G—YY—N————W—P——— | | |
| HP03494 | 43 | ELVHAGWEKCWSRRENRPYYFNRFTNQSLWEMPVLGQHD | (SEQ ID NO: 8) | |
| Npw38 | 46 | EGLPPSWYKVFDPSCGLPYYWNADTDLVSWLSPHDPNSV | (SEQ ID NO: 9) | BAA76400 |
| Yap_Human | 171 | VPLPAGWEMAKTSS.GQRYFLNHIDQTTTWQDPRKAMLS | (SEQ ID NO: 10) | P46937 |
| Yap_Chick-1 | 169 | VPLPPGWEMAKTPS.GQRYFLNHIDQTTTWQDPRKAMLS | (SEQ ID NO: 11) | P46936 |
| Yap_Mouse-1 | 156 | VPLPAGWEMAKTSS.GQRYFLNHNDQTTTWQDPRKAMLS | (SEQ ID NO: 12) | P46938 |
| Ned4_Mouse-1 | 40 | SPLPPGWEERQDVL.GRTYYVNHESRRTQWKRPSPDDDL | (SEQ ID NO: 13) | P46935 |
| Ned4_Human-1 | 218 | SPLPPGWEERQDIL.GRTYYVNHESRRTQWKRPTPQDNL | (SEQ ID NO: 14) | P46934 |
| Ned4_Mouse-2 | 196 | SGLPPGWEEKQDDR.GRSYYVDHNSKTTTWSKPTMQDDP | (SEQ ID NO: 15) | P46935 |
| Ned4_Human-2 | 375 | SGLPPGWEEKQDER.GRSYYVDHNSRTTTWTKPTVQATV | (SEQ ID NO: 16) | P46934 |
| Dmd_Human | 3055 | TSVQGPWERAISPN.KVPYYINHETQTTCWDHPKMTELY | (SEQ ID NO: 17) | P11532 |
| Dmd_Mouse | 3048 | TSVQGPWERAISPN.KVPYYINHETQTTCWDHPKMTELY | (SEQ ID NO: 18) | P11531 |
| FE65_Rat | 42 | SDLPAGWMRVQDTS.GTYYWHI.PTGTTQWEPPGRASPS | (SEQ ID NO: 19) | P46933 |

TABLE 1-continued

| Protein | Position | Amino Pod Sequence | | Accession No. |
|---|---|---|---|---|
| Msb1/Human | 249 | IVLPPNWKTARDPE.GKIYYYHVITRQTQWDPPTWESPG | (SEQ ID NO: 20) | |
| IQGA_Human | 679 | GDNNSKWVKHWVKG.GYYYYHNLETQEGGWDEPPNFVQN | (SEQ ID NO: 21) | P46940 |
| FBP11-1_Mouse | 1 | ......WTEHKSPD.GRTYYYNTETKQSTWEKPDDLKTP | (SEQ ID NO: 22) | U40747 |
| FBP11-2_Mouse | 36 | LLSKCPWKTYKSDS.GKPYYYNSQTKESRWAKP...... | (SEQ ID NO: 23) | U40747 |

(ii) Northern Blotting

Multi tissue Northern Blot (Clontech) having human tissue poly(A)+ RNA blotted thereon was used as an mRNA source. As the probe, an EcoRI-NotI fragment of full-length HP03494 cDNA, labeled with a radioisotope by a random primer labeling kit (Pharmacia), was used. The conditions for Northern blotting hybridization followed the protocol attached to the kit. An about 3-kb hybridization band was obtained from the heart, brain, placenta, lung, liver, skeletal muscle, kidney, pancreas, spleen, thymus, prostate, testicle, ovary, small intestine, colon and peripheral blood, suggesting that this protein is a housekeeping one.

(iii) Protein Synthesis by In Vitro Translation

A plasmid vector harboring the polynucleotide (cDNA) of this invention was used to perform in vitro transcription/translation by a $T_NT$ rabbit reticulocyte lysate kit (a product of Promega). The expression product was labeled with a radioisotope by adding [$^{35}$S] methionine. Any reaction was conducted according to the protocol attached to the kit. 2 µg of the plasmid was reacted at 30° C. for 90 minutes in a 25 µl reaction solution containing 12.5 µl TNT rabbit reticulocyte lysate, 0.5 µl buffer (attached to the kit), 2 µl amino acid mixture (not containing methionine), 2 µl (0.35 MBq/µl) of [$^{35}$S] methionine (Amersham), 0.5 µl of T7 RNA polymerase and 20 U of RNasin. Then, 2 µl SDS sampling buffer (125 mM Tris-HCl, pH 6.8, 120 mM 2-mercaptoethanol, 2% SDS solution, 0.025% bromophenol blue, 20% glycerol) was added to 3 µl of the reaction solution, and the mixture was treated by heating at 95° C. for 3 minutes and subjected to SDS-polyacrylamide gel electrophoresis. By autoradiography, the molecular weight of the translated product was determined. As a result, the translation product, which had a molecular weight of 80 kDa almost similar to the molecular weight (80,618) deduced from the ORF, was formed.

(iv) Expression of GST Fusion Protein in *E. coli*

The translated region was amplified by PCR where pHP03494 was used as a template while a 26-mer sense primer (SEQ ID NO: 4) starting at a translation initiation codon and having an EcoRI recognition site added thereto and a 26-mer antisense primer (SEQ ID NO: 5) terminating at a termination codon having a SalI recognition site added thereto were used respectively as primers. The PCR product was digested with restriction enzyme EcoRI and inserted into EcoRI site in vector pGEX-5X-1 (Pharmacia). After its nucleotide sequence was confirmed, the resulting plasmid was used for transforming *E. coli* BL21. The transformant was cultured at 37° C. for 5 hours in LB medium, and IPTG was added thereto at a final concentration of 0.4 mM, followed by culturing at 37° C. for 2.5 hours. The microorganism was separated by centrifugation and lysed in a lysing solution (50 mM Tris-HCl (pH 7.5), 1 mM EDTA-1% Triton X-100, 0.2% SDS, 0.2 mM PMSF), frozen once at −80° C., thawed, and disrupted by sonication. After centrifugation at 1000× g for 30 minutes, glutathione Sepharose 4B was added to the supernatant and incubated at 4° C. for 1 hour. After the beads were sufficiently washed, a fusion protein was eluted with an eluent (10 mM Tris-50 mM glutathione). As a result, a GST-HP03494 fusion protein having a molecular weight of about 110 kDa was obtained.

(v) Preparation of Antibody

Domestic rabbits were immunized with the above fusion protein as the antigen to give antiserum. First, an antiserum fraction precipitating by 40% saturation with ammonium sulfate was applied onto a GST affinity column to remove GST antibody. Then, the unadsorbed fraction was purified by a GST-HP03494-antigen column.

(vi) Western blotting

A lysate of human fibrosarcoma cell line HT-1080 was separated by SDS-PAGE, blotted onto a PVDF membrane, blocked for 1 hour at room temperature with 0.05% Tween 20-PBS (TPBS) containing 5% skim milk, and incubated with the antibody diluted 10,000-fold with TPBS. The sample was washed 3 times with TPBS and then incubated for 1 hour with horseradish peroxidase-labeled goat anti-rabbit IgG diluted 10,000-fold with TPBS. The sample was washed four times with TPBS and detected by luminescence with an ECL reagent (Amersham), to give a signal with a molecular weight of 80 kDa. This molecular weight agreed with the molecular weight of the in vitro translated protein product in the rabbit cell-free translation system.

(vii) Expression of GFP Fusion Protein

The translated region was amplified by PCR where pHP03494 was used as a template while a 26-mer sense primer (SEQ ID NO: 4) starting at a translation initiation codon having an EcoRI recognition site added thereto and a 26-mer antisense primer (SEQ ID NO: 5) terminating at a termination codon having a SalI recognition site added thereto were used respectively as primers. The PCR product was digested with restriction enzymes EcoRI and SalI and inserted into EcoRI site in GFP fusion protein expression vector pEGFP-C2 (Clontech). After the nucleotide sequence was confirmed, HeLa cells were transfected by the lipofection method with the resulting plasmid pEGFP-C2-HP03494. Under a fluorescence microscope, the cells transfected with pEGFP-C2 showed fluorescence on the whole of the cells, whereas the cells transfected with pEGFP-C2-HP03494 showed fluorescence on their nuclei only. This result indicated that HP03494 is a protein present in nucleus.

(viii) Binding to a C-Terminal Domain (CTD) of RNA Polymerase II

The translated region coding for WW domain was amplified by PCR where pHP03494 was used as a template while a 33-mer sense primer (SEQ ID NO: 6) starting at a translation initiation codon with a BamHI recognition site added thereto and a 33-mer antisense primer (SEQ ID NO: 7) terminating at a termination codon with an EcoRI recognition site added thereto were used respectively as primers. The PCR product was digested with restriction enzymes BamHI and EcoRI and then inserted into BamHI-EcoRI sites in vector pGEX-5X-1 (Pharmacia). The resulting plasmid was subjected to expression in *E. coli* in the same manner as in (iv), to give a fusion protein GST-HP03494WW consisting of GST and HP03494 WW domain, and this fusion protein was separated by SDS-PAGE, then transferred onto a PVDF membrane, incubated with $^{32}$P-labeled GST-CTD or $^{32}$P-labeled GST-pCTD (GST-phosphorylated CTD) phosphorylated depending on a nuclear extract (Hirose, Y and Manley, J. L., Nature, 395, 93–96, 1998), and detected by the Far Western method (Kaelin, Jr. et al., Cell, 70, 351–364, 1992). It was revealed that the WW domain on HP03494 binds more strongly to phosphorylated CTD. This result suggested that the protein of this invention is involved in regulating transcription.

INDUSTRIAL APPLICABILITY

This invention provides an isolated and purified human nuclear protein existing in human cell nucleus, a polynucleotide (human cDNA and genomic DNA fragment) encoding this protein, and an antibody against this nuclear protein. The protein and antibody of this invention are useful for diagnosis and therapy of morbid states such as cancers. By use of the present polynucleotide, the present protein can be expressed in a large amount. By screening a low-molecular compound binding to the present protein, a new type of pharmaceutical preparation such as antitumor agent can be searched for.

What is claimed is:

1. An isolated polynucleotide encoding a human nuclear protein comprising the amino acid sequence of SEQ ID NO:1, which comprises the nucleotide sequence of SEQ ID NO:2.

2. The polynucleotide of claim 1, consisting of the nucleotide sequence of SEQ ID NO:2.

3. An expression vector expressing the polynucleotide of claim 1 in in vitro translation or in host cells.

4. A transformed cell producing a human nuclear protein comprising the amino acid sequence of SEQ ID NO:1, which is a cell transformed with an expression vector which expresses the polynucleotide of claim 1.

5. An expression vector expressing the polynucleotide of claim 2 in in vitro translation or in host cells.

6. A transformed cell producing a human nuclear protein comprising the amino acid sequence of SEQ ID NO:1, which is a cell transformed with an expression vector which expresses a polynucleotide of claim 1.

* * * * *

SEQUENCE LISTING

<160> NUMBER OF SEQ ID NOS: 23

<210> SEQ ID NO 1
<211> LENGTH: 704
<212> TYPE: PRT
<213> ORGANISM: Homo sapiens

<400> SEQUENCE: 1

```
Met Ala Asn Glu Asn His Gly Ser Pro Arg Glu Glu Ala Ser Leu Leu
 1               5                  10                  15

Ser His Ser Pro Gly Thr Ser Asn Gln Ser Gln Pro Cys Ser Pro Lys
                20                  25                  30

Pro Ile Arg Leu Val Gln Asp Leu Pro Glu Glu Leu Val His Ala Gly
            35                  40                  45

Trp Glu Lys Cys Trp Ser Arg Arg Glu Asn Arg Pro Tyr Tyr Phe Asn
        50                  55                  60

Arg Phe Thr Asn Gln Ser Leu Trp Glu Met Pro Val Leu Gly Gln His
 65                  70                  75                  80

Asp Val Ile Ser Asp Pro Leu Gly Leu Asn Ala Thr Pro Leu Pro Gln
                85                  90                  95

Asp Ser Ser Leu Val Glu Thr Pro Pro Ala Glu Asn Lys Pro Arg Lys
            100                 105                 110

Arg Gln Leu Ser Glu Glu Gln Pro Ser Gly Asn Gly Val Lys Lys Pro
        115                 120                 125

Lys Ile Glu Ile Pro Val Thr Pro Thr Gly Gln Ser Val Pro Ser Ser
    130                 135                 140

Pro Ser Ile Pro Gly Thr Pro Thr Leu Lys Met Trp Gly Thr Ser Pro
145                 150                 155                 160

Glu Asp Lys Gln Gln Ala Ala Leu Leu Arg Pro Thr Glu Val Tyr Trp
                165                 170                 175

Asp Leu Asp Ile Gln Thr Asn Ala Val Ile Lys His Arg Gly Pro Ser
            180                 185                 190

Glu Val Leu Pro Pro His Pro Glu Val Glu Leu Leu Arg Ser Gln Leu
        195                 200                 205

Ile Leu Lys Leu Arg Gln His Tyr Arg Glu Leu Cys Gln Gln Arg Glu
    210                 215                 220

Gly Ile Glu Pro Pro Arg Glu Ser Phe Asn Arg Trp Met Leu Glu Arg
225                 230                 235                 240
```

-continued

Lys Val Val Asp Lys Gly Ser Asp Pro Leu Leu Pro Ser Asn Cys Glu
            245                 250                 255

Pro Val Val Ser Pro Ser Met Phe Arg Glu Ile Met Asn Asp Ile Pro
            260                 265                 270

Ile Arg Leu Ser Arg Ile Lys Phe Arg Glu Glu Ala Lys Arg Leu Leu
            275                 280                 285

Phe Lys Tyr Ala Glu Ala Ala Arg Arg Leu Ile Glu Ser Arg Ser Ala
    290                 295                 300

Ser Pro Asp Ser Arg Lys Val Val Lys Trp Asn Val Glu Asp Thr Phe
305                 310                 315                 320

Ser Trp Leu Arg Lys Asp His Ser Ala Ser Lys Glu Asp Tyr Met Asp
                325                 330                 335

Arg Leu Glu His Leu Arg Arg Gln Cys Gly Pro His Val Ser Ala Ala
            340                 345                 350

Ala Lys Asp Ser Val Glu Gly Ile Cys Ser Lys Ile Tyr His Ile Ser
            355                 360                 365

Leu Glu Tyr Val Lys Arg Ile Arg Glu Lys His Leu Ala Ile Leu Lys
    370                 375                 380

Glu Asn Asn Ile Ser Glu Val Glu Ala Pro Glu Val Glu Pro Arg
385                 390                 395                 400

Leu Val Tyr Cys Tyr Pro Val Arg Leu Ala Val Ser Ala Pro Pro Met
                405                 410                 415

Pro Ser Val Glu Met His Met Glu Asn Asn Val Val Cys Ile Arg Tyr
            420                 425                 430

Lys Gly Glu Met Val Lys Val Ser Arg Asn Tyr Phe Ser Lys Leu Trp
            435                 440                 445

Leu Leu Tyr Arg Tyr Ser Cys Ile Asp Asp Ser Ala Phe Glu Arg Phe
    450                 455                 460

Leu Pro Arg Val Trp Cys Leu Leu Arg Arg Tyr Gln Met Met Phe Gly
465                 470                 475                 480

Val Gly Leu Tyr Glu Gly Thr Gly Leu Gln Gly Ser Leu Pro Val His
                485                 490                 495

Val Phe Glu Ala Leu His Arg Leu Phe Gly Val Ser Phe Glu Cys Phe
            500                 505                 510

Ala Ser Pro Leu Asn Cys Tyr Phe Arg Gln Tyr Cys Ser Ala Phe Pro
            515                 520                 525

Asp Thr Asp Gly Tyr Phe Gly Ser Arg Gly Pro Cys Leu Asp Phe Ala
    530                 535                 540

Pro Leu Ser Gly Ser Phe Glu Ala Asn Pro Pro Phe Cys Glu Glu Leu
545                 550                 555                 560

Met Asp Ala Met Val Ser His Phe Glu Arg Leu Leu Glu Ser Ser Pro
                565                 570                 575

Glu Pro Leu Ser Phe Ile Val Phe Ile Pro Glu Trp Arg Glu Pro Pro
            580                 585                 590

Thr Pro Ala Leu Thr Arg Met Glu Gln Ser Arg Phe Lys Arg His Gln
            595                 600                 605

Leu Ile Leu Pro Ala Phe Glu His Glu Tyr Arg Ser Gly Ser Gln His
    610                 615                 620

Ile Cys Lys Lys Glu Glu Met His Tyr Lys Ala Val His Asn Thr Ala
625                 630                 635                 640

Val Leu Phe Leu Gln Asn Asp Pro Gly Phe Ala Lys Trp Ala Pro Thr
                645                 650                 655

Pro Glu Arg Leu Gln Glu Leu Ser Ala Ala Tyr Arg Gln Ser Gly Arg

|  |  | 660 |  |  | 665 |  |  | 670 |  |  |  |
|--|--|--|--|--|--|--|--|--|--|--|--|

Ser His Ser Ser Gly Ser Ser Ser Ser Ser Glu Ala Lys Asp
        675                  680                  685

Arg Asp Ser Gly Arg Glu Gln Gly Pro Ser Arg Glu Pro His Pro Thr
  690                        695                      700

<210> SEQ ID NO 2
<211> LENGTH: 2112
<212> TYPE: DNA
<213> ORGANISM: Homo sapiens

<400> SEQUENCE: 2

| atggccaatg | agaatcacgg | cagccccgg | gaggaagcgt | ccctgctgag | tcactcccca | 60 |
|--|--|--|--|--|--|--|
| ggtacctcca | atcagagcca | gccctgttct | ccaaagccaa | tccgcctggt | tcaggacctc | 120 |
| ccagaggagc | tggtgcatgc | aggctgggag | aagtgctgga | gccggaggga | gaatcgtccc | 180 |
| tactacttca | accgattcac | caaccagtcc | ctgtgggaga | tgcccgtgct | ggggcagcac | 240 |
| gatgtgattt | cggaccettt | ggggctgaat | gcgaccccac | tgccccaaga | ctcaagcttg | 300 |
| gtggaaactc | cccggctga | gaacaagccc | agaaagcggc | agctctcgga | gagcagcca | 360 |
| agcggcaatg | gtgtgaagaa | gcccaagatt | gaaatcccag | tgacacccac | aggccagtcg | 420 |
| gtgcccagct | cccccagtat | cccaggaacc | caacgctga | gatgtgggg | tacgtcccct | 480 |
| gaagataaac | agcaggcagc | tctcctacga | cccactgagg | tctactggga | cctggacatc | 540 |
| cagaccaatg | ctgtcatcaa | gcaccggggg | ccttcagagg | tgctgccccc | gcatcccgaa | 600 |
| gtggaactgc | tccgctctca | gctcatcctg | aagcttcggc | agcactatcg | ggagctgtgc | 660 |
| cagcagcgag | agggcattga | gcctccacg | gagtcttca | accgctggat | gctggagcgc | 720 |
| aaggtggtag | acaaaggatc | tgacccctg | ttgcccagca | actgtgaacc | agtcgtgtca | 780 |
| ccttccatgt | ttcgtgaaat | catgaacgac | attcctatca | ggttatcccg | aatcaagttc | 840 |
| cgggaggaag | ccaagcgcct | gctctttaaa | tatgcggagg | ccgccaggcg | gctcatcgag | 900 |
| tccaggagtg | catcccctga | cagtaggaag | gtggtcaaat | ggaatgtgga | agacaccttt | 960 |
| agctggcttc | ggaaggacca | ctcagcctcc | aaggaggact | acatggatcg | cctggagcat | 1020 |
| ctgcggaggc | agtgtggccc | ccacgtctcg | gccgcagcca | aggactccgt | ggaaggcatc | 1080 |
| tgcagtaaga | tctaccacat | ctccctggag | tacgtcaaac | ggatccgaga | gaagcacctt | 1140 |
| gccatcctca | aggaaaacaa | catctcagag | gaggtggagg | ccctgaggt | ggagccccgc | 1200 |
| ctagtgtact | gctacccagt | ccggctggct | gtgtctgcac | cgcccatgcc | cagcgtggag | 1260 |
| atgcacatgg | agaacaacgt | ggtctgcatc | cggtataagg | gagagatggt | caaggtcagc | 1320 |
| cgcaactact | tcagcaagct | gtggctcctt | taccgctaca | gctgcattga | tgactctgcc | 1380 |
| tttgagaggt | tcctgccccg | ggtctggtgt | cttctccgac | ggtaccagat | gatgttcggc | 1440 |
| gtgggcctct | acgaggggac | tggcctgcag | ggatcgctgc | ctgtgcatgt | ctttgaggcc | 1500 |
| ctccaccgac | tctttggcgt | cagcttcgag | tgcttcgcct | caccctcaa | ctgctacttc | 1560 |
| cgccagtact | gttctgcctt | ccccgacaca | gacggctact | ttggctcccg | cgggccctgc | 1620 |
| ctagactttg | ctccactgag | tggttcattt | gaggccaacc | ctccttctg | cgaggagctc | 1680 |
| atggatgcca | tggtctctca | ctttgagaga | ctgcttgaga | gctcaccgga | gccctgtcc | 1740 |
| ttcatcgtgt | tcatccctga | gtggcgggaa | ccccaacac | cagcgctcac | ccgcatggag | 1800 |
| cagagccgct | tcaaacgcca | ccagttgatc | ctgcctgcct | ttgagcatga | gtaccgcagt | 1860 |
| ggctcccagc | acatctgcaa | gaaggaggaa | atgcactaca | aggccgtcca | caacacggct | 1920 |

```
gtgctcttcc tacagaacga ccctggcttt gccaagtggg cgccgacgcc tgaacggctg    1980
caggagctga gtgctgccta ccggcagtca ggccgcagcc acagctctgg ttcttcctca    2040
tcgtcctcct cggaggccaa ggaccgggac tcgggccgtg agcagggtcc tagccgcgag    2100
cctcacccca ct                                                         2112

<210> SEQ ID NO 3
<211> LENGTH: 2669
<212> TYPE: DNA
<213> ORGANISM: Homo sapiens
<220> FEATURE:
<221> NAME/KEY: CDS
<222> LOCATION: (292)..(2406)

<400> SEQUENCE: 3
acacaagatg gcggcagcgg cgctggggag ggcgaggcgg aggcggcaaa acgggcggtc     60
gagcagaacg tgtagccgcg tcccctccag tccgctccgg gcagctgctg atgcaaggaa    120 tccccctgggc tcccgtccac tccactgctg accagcccat tcgcctgtgc tgagtcttcc  180
tgcaggcctt tccttgcctc tgtgggaccc tgtggggtc catccggctg gagaagaaaa    240
gcctctcatg ctaacgttgc agaccccaga gggtcctgtg tgggtgtgga g atg gcc    297
                                                         Met Ala
                                                           1 aat gag aat cac ggc agc ccc cgg gag gaa gcg tcc ctg ctg agt cac    345
Asn Glu Asn His Gly Ser Pro Arg Glu Glu Ala Ser Leu Leu Ser His
        5                   10                  15 tcc cca ggt acc tcc aat cag agc cag ccc tgt tct cca aag cca atc    393
Ser Pro Gly Thr Ser Asn Gln Ser Gln Pro Cys Ser Pro Lys Pro Ile
    20                  25                  30 cgc ctg gtt cag gac ctc cca gag gag ctg gtg cat gca ggc tgg gag    441
Arg Leu Val Gln Asp Leu Pro Glu Glu Leu Val His Ala Gly Trp Glu
35                  40                  45                  50 aag tgc tgg agc cgg agg gag aat cgt ccc tac tac ttc aac cga ttc    489
Lys Cys Trp Ser Arg Arg Glu Asn Arg Pro Tyr Tyr Phe Asn Arg Phe
                55                  60                  65 acc aac cag tcc ctg tgg gag atg ccc gtg ctg ggg cag cac gat gtg    537
Thr Asn Gln Ser Leu Trp Glu Met Pro Val Leu Gly Gln His Asp Val
            70                  75                  80 att tcg gac cct ttg ggg ctg aat gcg acc cca ctg ccc caa gac tca    585
Ile Ser Asp Pro Leu Gly Leu Asn Ala Thr Pro Leu Pro Gln Asp Ser
        85                  90                  95 agc ttg gtg gaa act ccc ccg gct gag aac aag ccc aga aag cgg cag    633
Ser Leu Val Glu Thr Pro Pro Ala Glu Asn Lys Pro Arg Lys Arg Gln
    100                 105                 110 ctc tcg gaa gag cag cca agc ggc aat ggt gtg aag aag ccc aag att    681
Leu Ser Glu Glu Gln Pro Ser Gly Asn Gly Val Lys Lys Pro Lys Ile
115                 120                 125                 130 gaa atc cca gtg aca ccc aca ggc cag tcg gtg ccc agc tcc ccc agt    729
Glu Ile Pro Val Thr Pro Thr Gly Gln Ser Val Pro Ser Ser Pro Ser
                135                 140                 145 atc cca gga acc cca acg ctg aag atg tgg ggt acg tcc cct gaa gat    777
Ile Pro Gly Thr Pro Thr Leu Lys Met Trp Gly Thr Ser Pro Glu Asp
            150                 155                 160 aaa cag cag gca gct ctc cta cga ccc act gag gtc tac tgg gac ctg    825
Lys Gln Gln Ala Ala Leu Leu Arg Pro Thr Glu Val Tyr Trp Asp Leu
        165                 170                 175 gac atc cag acc aat gct gtc atc aag cac cgg ggg cct tca gag gtg    873
Asp Ile Gln Thr Asn Ala Val Ile Lys His Arg Gly Pro Ser Glu Val
    180                 185                 190
```

-continued

| | |
|---|---|
| ctg ccc ccg cat ccc gaa gtg gaa ctg ctc cgc tct cag ctc atc ctg<br>Leu Pro Pro His Pro Glu Val Glu Leu Leu Arg Ser Gln Leu Ile Leu<br>195                    200                    205                    210 | 921 |
| aag ctt cgg cag cac tat cgg gag ctg tgc cag cag cga gag ggc att<br>Lys Leu Arg Gln His Tyr Arg Glu Leu Cys Gln Gln Arg Glu Gly Ile<br>                    215                    220                    225 | 969 |
| gag cct cca cgg gag tct ttc aac cgc tgg atg ctg gag cgc aag gtg<br>Glu Pro Pro Arg Glu Ser Phe Asn Arg Trp Met Leu Glu Arg Lys Val<br>                230                    235                    240 | 1017 |
| gta gac aaa gga tct gac ccc ctg ttg ccc agc aac tgt gaa cca gtc<br>Val Asp Lys Gly Ser Asp Pro Leu Leu Pro Ser Asn Cys Glu Pro Val<br>          245                    250                    255 | 1065 |
| gtg tca cct tcc atg ttt cgt gaa atc atg aac gac att cct atc agg<br>Val Ser Pro Ser Met Phe Arg Glu Ile Met Asn Asp Ile Pro Ile Arg<br>260                    265                    270 | 1113 |
| tta tcc cga atc aag ttc cgg gag gaa gcc aag cgc ctg ctc ttt aaa<br>Leu Ser Arg Ile Lys Phe Arg Glu Glu Ala Lys Arg Leu Leu Phe Lys<br>275                    280                    285                    290 | 1161 |
| tat gcg gag gcc gcc agg cgg ctc atc gag tcc agg agt gca tcc cct<br>Tyr Ala Glu Ala Ala Arg Arg Leu Ile Glu Ser Arg Ser Ala Ser Pro<br>                    295                    300                    305 | 1209 |
| gac agt agg aag gtg gtc aaa tgg aat gtg gaa gac acc ttt agc tgg<br>Asp Ser Arg Lys Val Val Lys Trp Asn Val Glu Asp Thr Phe Ser Trp<br>                310                    315                    320 | 1257 |
| ctt cgg aag gac cac tca gcc tcc aag gag gac tac atg gat cgc ctg<br>Leu Arg Lys Asp His Ser Ala Ser Lys Glu Asp Tyr Met Asp Arg Leu<br>          325                    330                    335 | 1305 |
| gag cat ctg cgg agg cag tgt ggc ccc cac gtc tcg gcc gca gcc aag<br>Glu His Leu Arg Arg Gln Cys Gly Pro His Val Ser Ala Ala Ala Lys<br>340                    345                    350 | 1353 |
| gac tcc gtg gaa ggc atc tgc agt aag atc tac cac atc tcc ctg gag<br>Asp Ser Val Glu Gly Ile Cys Ser Lys Ile Tyr His Ile Ser Leu Glu<br>355                    360                    365                    370 | 1401 |
| tac gtc aaa cgg atc cga gag aag cac ctt gcc atc ctc aag gaa aac<br>Tyr Val Lys Arg Ile Arg Glu Lys His Leu Ala Ile Leu Lys Glu Asn<br>                375                    380                    385 | 1449 |
| aac atc tca gag gag gtg gag gcc cct gag gtg gag ccc cgc cta gtg<br>Asn Ile Ser Glu Glu Val Glu Ala Pro Glu Val Glu Pro Arg Leu Val<br>                    390                    395                    400 | 1497 |
| tac tgc tac cca gtc cgg ctg gct gtg tct gca ccg ccc atg ccc agc<br>Tyr Cys Tyr Pro Val Arg Leu Ala Val Ser Ala Pro Pro Met Pro Ser<br>          405                    410                    415 | 1545 |
| gtg gag atg cac atg gag aac aac gtg gtc tgc atc cgg tat aag gga<br>Val Glu Met His Met Glu Asn Asn Val Val Cys Ile Arg Tyr Lys Gly<br>420                    425                    430 | 1593 |
| gag atg gtc aag gtc agc cgc aac tac ttc agc aag ctg tgg ctc ctt<br>Glu Met Val Lys Val Ser Arg Asn Tyr Phe Ser Lys Leu Trp Leu Leu<br>435                    440                    445                    450 | 1641 |
| tac cgc tac agc tgc att gat gac tct gcc ttt gag agg ttc ctg ccc<br>Tyr Arg Tyr Ser Cys Ile Asp Asp Ser Ala Phe Glu Arg Phe Leu Pro<br>                455                    460                    465 | 1689 |
| cgg gtc tgg tgt ctt ctc cga cgg tac cag atg atg ttc ggc gtg ggc<br>Arg Val Trp Cys Leu Leu Arg Arg Tyr Gln Met Met Phe Gly Val Gly<br>                470                    475                    480 | 1737 |
| ctc tac gag ggg act ggc ctg cag gga tcg ctg cct gtg cat gtc ttt<br>Leu Tyr Glu Gly Thr Gly Leu Gln Gly Ser Leu Pro Val His Val Phe<br>          485                    490                    495 | 1785 |
| gag gcc ctc cac cga ctc ttt ggc gtc agc ttc gag tgc ttc gcc tca<br>Glu Ala Leu His Arg Leu Phe Gly Val Ser Phe Glu Cys Phe Ala Ser | 1833 |

| | | | | | | | | | | | | | | |
|---|---|---|---|---|---|---|---|---|---|---|---|---|---|---|
| | | 500 | | | | 505 | | | | | 510 | | | |
| ccc | ctc | aac | tgc | tac | ttc | cgc | cag | tac | tgt | tct | gcc | ttc | ccc | gac aca | 1881 |
| Pro | Leu | Asn | Cys | Tyr | Phe | Arg | Gln | Tyr | Cys | Ser | Ala | Phe | Pro | Asp Thr |
| 515 | | | | | 520 | | | | | 525 | | | | 530 |
| gac | ggc | tac | ttt | ggc | tcc | cgc | ggg | ccc | tgc | cta | gac | ttt | gct | cca ctg | 1929 |
| Asp | Gly | Tyr | Phe | Gly | Ser | Arg | Gly | Pro | Cys | Leu | Asp | Phe | Ala | Pro Leu |
| | | | | 535 | | | | | 540 | | | | | 545 |
| agt | ggt | tca | ttt | gag | gcc | aac | cct | ccc | ttc | tgc | gag | gag | ctc | atg gat | 1977 |
| Ser | Gly | Ser | Phe | Glu | Ala | Asn | Pro | Pro | Phe | Cys | Glu | Glu | Leu | Met Asp |
| | | | 550 | | | | | 555 | | | | | 560 | |
| gcc | atg | gtc | tct | cac | ttt | gag | aga | ctg | ctt | gag | agc | tca | ccg | gag ccc | 2025 |
| Ala | Met | Val | Ser | His | Phe | Glu | Arg | Leu | Leu | Glu | Ser | Ser | Pro | Glu Pro |
| | | 565 | | | | | 570 | | | | | 575 | | |
| ctg | tcc | ttc | atc | gtg | ttc | atc | cct | gag | tgg | cgg | gaa | ccc | cca | aca cca | 2073 |
| Leu | Ser | Phe | Ile | Val | Phe | Ile | Pro | Glu | Trp | Arg | Glu | Pro | Pro | Thr Pro |
| | 580 | | | | | 585 | | | | | 590 | | | |
| gcg | ctc | acc | cgc | atg | gag | cag | agc | cgc | ttc | aaa | cgc | cac | cag | ttg atc | 2121 |
| Ala | Leu | Thr | Arg | Met | Glu | Gln | Ser | Arg | Phe | Lys | Arg | His | Gln | Leu Ile |
| 595 | | | | | 600 | | | | | 605 | | | | 610 |
| ctg | cct | gcc | ttt | gag | cat | gag | tac | cgc | agt | ggc | tcc | cag | cac | atc tgc | 2169 |
| Leu | Pro | Ala | Phe | Glu | His | Glu | Tyr | Arg | Ser | Gly | Ser | Gln | His | Ile Cys |
| | | | | 615 | | | | | 620 | | | | | 625 |
| aag | aag | gag | gaa | atg | cac | tac | aag | gcc | gtc | cac | aac | acg | gct | gtg ctc | 2217 |
| Lys | Lys | Glu | Glu | Met | His | Tyr | Lys | Ala | Val | His | Asn | Thr | Ala | Val Leu |
| | | | 630 | | | | | 635 | | | | | 640 | |
| ttc | cta | cag | aac | gac | cct | ggc | ttt | gcc | aag | tgg | gcg | ccg | acg | cct gaa | 2265 |
| Phe | Leu | Gln | Asn | Asp | Pro | Gly | Phe | Ala | Lys | Trp | Ala | Pro | Thr | Pro Glu |
| | | 645 | | | | | 650 | | | | | 655 | | |
| cgg | ctg | cag | gag | ctg | agt | gct | gcc | tac | cgg | cag | tca | ggc | cgc | agc cac | 2313 |
| Arg | Leu | Gln | Glu | Leu | Ser | Ala | Ala | Tyr | Arg | Gln | Ser | Gly | Arg | Ser His |
| | 660 | | | | | 665 | | | | | 670 | | | |
| agc | tct | ggt | tct | tcc | tca | tcg | tcc | tcc | tcg | gag | gcc | aag | gac | cgg gac | 2361 |
| Ser | Ser | Gly | Ser | Ser | Ser | Ser | Ser | Ser | Ser | Glu | Ala | Lys | Asp | Arg Asp |
| 675 | | | | | 680 | | | | | 685 | | | | 690 |
| tcg | ggc | cgt | gag | cag | ggt | cct | agc | cgc | gag | cct | cac | ccc | act | taa | 2406 |
| Ser | Gly | Arg | Glu | Gln | Gly | Pro | Ser | Arg | Glu | Pro | His | Pro | Thr | | |
| | | | | 695 | | | | | 700 | | | | | | | catatcctgc ggggaggagg agccccaggg gtgctagtct ggactgctgg gactcgggcc 2466 cctggggcct cagagggacc ccggctgcca ctgacatatg aagattatgg ttctgccagg 2526 gctcccctcc ctgcctgtcc ccaagtcctc acctcaaact ccctccaagt cccatgtata 2586 taggtcctga tgccttccca accccgcccc tcaccctgtt gccaccttgt ttcatttgta 2646 aaaggaaata cagaaacccc ccc 2669

<210> SEQ ID NO 4
<211> LENGTH: 26
<212> TYPE: DNA
<213> ORGANISM: Artificial sequence
<220> FEATURE:
<223> OTHER INFORMATION: Synthesized oligonucleotide

<400> SEQUENCE: 4
ccgaattcat ggccaatgag aatcac                                      26

<210> SEQ ID NO 5
<211> LENGTH: 26
<212> TYPE: DNA
<213> ORGANISM: Artificial sequence
<220> FEATURE:
<223> OTHER INFORMATION: Synthesized oligonucleotide -continued

<400> SEQUENCE: 5
ccgtcgactt aagtggggtg aggctc                                          26

<210> SEQ ID NO 6
<211> LENGTH: 34
<212> TYPE: DNA
<213> ORGANISM: Artificial sequence
<220> FEATURE:
<223> OTHER INFORMATION: Synthesized oligonucleotide

<400> SEQUENCE: 6
cgaggatccg ttcaggacct cccagaggac gcta                                 34

<210> SEQ ID NO 7
<211> LENGTH: 33
<212> TYPE: DNA
<213> ORGANISM: Artificial sequence
<220> FEATURE:
<223> OTHER INFORMATION: Synthesized oligonucleotide

<400> SEQUENCE: 7
cgagaattcc gaaatcacat cgtgctgccc cag                                  33

<210> SEQ ID NO 8
<211> LENGTH: 39
<212> TYPE: PRT
<213> ORGANISM: HPO3494

<400> SEQUENCE: 8

Glu Leu Val His Ala Gly Trp Glu Lys Cys Trp Ser Arg Arg Glu Asn
1               5                   10                  15

Arg Pro Tyr Tyr Phe Asn Arg Phe Thr Asn Gln Ser Leu Trp Glu Met
            20                  25                  30

Pro Val Leu Gly Gln His Asp
        35

<210> SEQ ID NO 9
<211> LENGTH: 39
<212> TYPE: PRT
<213> ORGANISM: Npw38

<400> SEQUENCE: 9

Glu Gly Leu Pro Pro Ser Trp Tyr Lys Val Phe Asp Pro Ser Cys Gly
1               5                   10                  15

Leu Pro Tyr Tyr Trp Asn Ala Asp Thr Asp Leu Val Ser Trp Leu Ser
            20                  25                  30

Pro His Asp Pro Asn Ser Val
        35

<210> SEQ ID NO 10
<211> LENGTH: 38
<212> TYPE: PRT
<213> ORGANISM: Yap_Human

<400> SEQUENCE: 10

Val Pro Leu Pro Ala Gly Trp Glu Met Ala Lys Thr Ser Ser Gly Gln
1               5                   10                  15

Arg Tyr Phe Leu Asn His Ile Asp Gln Thr Thr Thr Trp Gln Asp Pro
            20                  25                  30

Arg Lys Ala Met Leu Ser
        35

```
<210> SEQ ID NO 11
<211> LENGTH: 38
<212> TYPE: PRT
<213> ORGANISM: Yap_chick-1

<400> SEQUENCE: 11

Val Pro Leu Pro Pro Gly Trp Glu Met Ala Lys Thr Pro Ser Gly Gln
1               5                   10                  15

Arg Tyr Phe Leu Asn His Ile Asp Gln Thr Thr Thr Trp Gln Asp Pro
            20                  25                  30

Arg Lys Ala Met Leu Ser
        35

<210> SEQ ID NO 12
<211> LENGTH: 38
<212> TYPE: PRT
<213> ORGANISM: Yap_mouse-1

<400> SEQUENCE: 12

Val Pro Leu Pro Ala Gly Trp Glu Met Ala Lys Thr Ser Ser Gly Gln
1               5                   10                  15

Arg Tyr Phe Leu Asn His Asn Asp Gln Thr Thr Thr Trp Gln Asp Pro
            20                  25                  30

Arg Lys Ala Met Leu Ser
        35

<210> SEQ ID NO 13
<211> LENGTH: 38
<212> TYPE: PRT
<213> ORGANISM: Ned4_Mouse-1

<400> SEQUENCE: 13

Ser Pro Leu Pro Pro Gly Trp Glu Glu Arg Gln Asp Val Leu Gly Arg
1               5                   10                  15

Thr Tyr Tyr Val Asn His Glu Ser Arg Arg Thr Gln Trp Lys Arg Pro
            20                  25                  30

Ser Pro Asp Asp Asp Leu
        35

<210> SEQ ID NO 14
<211> LENGTH: 38
<212> TYPE: PRT
<213> ORGANISM: Ned4_Human-1

<400> SEQUENCE: 14

Ser Pro Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro Gln Asp Asn Leu
        35

<210> SEQ ID NO 15
<211> LENGTH: 38
<212> TYPE: PRT
<213> ORGANISM: Ned4_Mouse-2

<400> SEQUENCE: 15

Ser Gly Leu Pro Pro Gly Trp Glu Glu Lys Gln Asp Asp Arg Gly Arg
1               5                   10                  15
```

Ser Tyr Tyr Val Asp His Asn Ser Lys Thr Thr Thr Trp Ser Lys Pro
            20                  25                  30

Thr Met Gln Asp Asp Pro
            35

<210> SEQ ID NO 16
<211> LENGTH: 38
<212> TYPE: PRT
<213> ORGANISM: Ned4_Human-2

<400> SEQUENCE: 16

Ser Gly Leu Pro Pro Gly Trp Glu Glu Lys Gln Asp Glu Arg Gly Arg
1               5                   10                  15

Ser Tyr Tyr Val Asp His Asn Ser Arg Thr Thr Thr Trp Thr Lys Pro
            20                  25                  30

Thr Val Gln Ala Thr Val
            35

<210> SEQ ID NO 17
<211> LENGTH: 38
<212> TYPE: PRT
<213> ORGANISM: Dmd_Human

<400> SEQUENCE: 17

Thr Ser Val Gln Gly Pro Trp Glu Arg Ala Ile Ser Pro Asn Lys Val
1               5                   10                  15

Pro Tyr Tyr Ile Asn His Glu Thr Gln Thr Thr Cys Trp Asp His Pro
            20                  25                  30

Lys Met Thr Glu Leu Tyr
            35

<210> SEQ ID NO 18
<211> LENGTH: 38
<212> TYPE: PRT
<213> ORGANISM: Dmd_Mouse

<400> SEQUENCE: 18

Thr Ser Val Gln Gly Pro Trp Glu Arg Ala Ile Ser Pro Asn Lys Val
1               5                   10                  15

Pro Tyr Tyr Ile Asn His Glu Thr Gln Thr Thr Cys Trp Asp His Pro
            20                  25                  30

Lys Met Thr Glu Leu Tyr
            35

<210> SEQ ID NO 19
<211> LENGTH: 37
<212> TYPE: PRT
<213> ORGANISM: FE65_Rat

<400> SEQUENCE: 19

Ser Asp Leu Pro Ala Gly Trp Met Arg Val Gln Asp Thr Ser Gly Thr
1               5                   10                  15

Tyr Tyr Trp His Ile Pro Thr Gly Thr Thr Gln Trp Glu Pro Pro Gly
            20                  25                  30

Arg Ala Ser Pro Ser
            35

<210> SEQ ID NO 20
<211> LENGTH: 38
<212> TYPE: PRT

```
<213> ORGANISM: Msb1/Human

<400> SEQUENCE: 20

Ile Val Leu Pro Pro Asn Trp Lys Thr Ala Arg Asp Pro Glu Gly Lys
1               5                   10                  15

Ile Tyr Tyr Tyr His Val Ile Thr Arg Gln Thr Gln Trp Asp Pro Pro
                20                  25                  30

Thr Trp Glu Ser Pro Gly
            35

<210> SEQ ID NO 21
<211> LENGTH: 38
<212> TYPE: PRT
<213> ORGANISM: I QGA_Human

<400> SEQUENCE: 21

Gly Asp Asn Asn Ser Lys Trp Val Lys His Trp Val Lys Gly Gly Tyr
1               5                   10                  15

Tyr Tyr Tyr His Asn Leu Glu Thr Gln Glu Gly Gly Trp Asp Glu Pro
                20                  25                  30

Pro Asn Phe Val Gln Asn
            35

<210> SEQ ID NO 22
<211> LENGTH: 32
<212> TYPE: PRT
<213> ORGANISM: FBP11-1_Mouse

<400> SEQUENCE: 22

Trp Thr Glu His Lys Ser Pro Asp Gly Arg Thr Tyr Tyr Tyr Asn Thr
1               5                   10                  15

Glu Thr Lys Gln Ser Thr Trp Glu Lys Pro Asp Asp Leu Lys Thr Pro
                20                  25                  30

<210> SEQ ID NO 23
<211> LENGTH: 32
<212> TYPE: PRT
<213> ORGANISM: FBP11-2_Mouse

<400> SEQUENCE: 23

Leu Leu Ser Lys Cys Pro Trp Lys Thr Tyr Lys Ser Asp Ser Gly Lys
1               5                   10                  15

Pro Tyr Tyr Tyr Asn Ser Gln Thr Lys Glu Ser Arg Trp Ala Lys Pro
                20                  25                  30
```